United States Patent [19]

Dixon

[11] Patent Number: 4,507,287

[45] Date of Patent: Mar. 26, 1985

[54] PREPARATION AND METHOD FOR THE TREATMENT OF ACNE

[76] Inventor: Glen J. Dixon, 1476 Stoneleigh Hills Rd., Lithonia, Ga. 30058

[21] Appl. No.: 505,784

[22] Filed: Jun. 20, 1983

[51] Int. Cl.³ ............................................. A61K 31/70
[52] U.S. Cl. ...................................... 514/43; 514/46; 514/859; 514/947
[58] Field of Search ................ 424/358, 227, 181, 180, 424/251; 536/26, 23

[56] References Cited

U.S. PATENT DOCUMENTS

| | | | |
|---|---|---|---|
| 3,551,554 | 12/1970 | Herschler | 424/141 |
| 3,711,602 | 1/1973 | Herschler . | |
| 3,743,727 | 7/1973 | Herschler . | |
| 4,081,534 | 3/1978 | Elion et al. | 536/26 |
| 4,150,114 | 4/1979 | Smith | 424/60 |
| 4,199,574 | 4/1980 | Schaeffer . | |
| 4,211,771 | 7/1980 | Witkowski et al. | 536/23 |

OTHER PUBLICATIONS

Chemical Abstracts, vol. 93; (1980), #101442w; Klein et al.
The Merck Index; 9th edition, (1976), #3602, 7991, 8913 and A15.
Dixon et al., 1969, "Antiviral Activity of 9-B-D-Arabinofuranosyladenine, V. Activity Against Intracerebral Vaccina Virus Infections in Mic," *Antimicrobial Agents and Chemotherapy*, pp. 172–179.
Sidwell et al., 1969, "Antiviral Activity of 9-B-D-Arabinofuranosyladenine, II. Activity Against Herpes Simplex Keratitis in Hamsters", *Antimicrobial Agents and Chemotherapy*, pp. 148–154.
Schardein et al., 1969, "Antiviral Activity of 9-B-D-Arabinofuranosyladenine, III. Reduction in Evidence of Encephalitis in Treated Herpes Simplex--Infected Hamsters", *Antimicrobial Agents and Chemotherapy*, pp. 155–160.
Sloan et al., 1969, "Antiviral Activity of 9-B-D-Arabinofuranosyladenine, IV. Activity Against Intracerebral Herpes Simplex Virus Infections in Mice," *Antimicrobial Agents and Chemotherapy*, pp. 161–171.
Hilton et al., Feb. 1978, "A Trial of Adenine Arabinoside in Genital Herpes," *British Journal of Veneral Diseases*, pp. 50–52.
Goodman et al., 1975, "Prospective Double-Blind Evaluation of Topical Adenine Arabinoside in Male Herpes Progenitalis," *Antimicrobial Agents and Chemotherapy*, vol. 8, No. 6, pp. 693–697.
MacCallum et al., Oct. 1, 1966, "Herpes Simplex Virus Skin Infection in Man Treated with Idoxuridine in Dimethyl Sulphoxide, Results of Double-Blind Controlled Trial," *British Medical Journal*, pp. 805–807.
Turnbull et al., Nov. 1969, "The Enhancing Effect of Dimethylsulfoxide Vehicle upon the Anti-Viral Actions of 5-Iododeoxyuridine," *New Zealand Medical Journal*, pp. 317–320.
Juel-Jensen et al., Dec. 1970, "Treatment of Zoster with Idoxuridine in Dimethyl Sulphoxide, Results of Two Double-Blind Controlled Trials," *British Medical Journal*, vol. 4, pp. 776–780.
Thormann et al., 1980, "Contact Allergy to Idoxuridine, Sensitization Following Treatment of Herpes Zoster," *Contact Dermatitis*, vol. 6, pp. 170–171.
Burton et al., Nov. 25, 1981, "On Trial, A Multicentre Trial of Zostrum (5 Percent Idoxuridine in Dimethylsulphoxide) in Herpes Zoster," *New Zealand Medical Journal*, pp. 384–386.
Silvestri et al., Aug. 27, 1982, "Ineffectiveness of Topical Idoxuridine in Dimethyl Sulfoxide for Therapy for Genital Herpes," *JAMA*, vol. 248, No. 8, pp. 953–959.
Spruance et al., 1983, "Dimethyl Sulfoxide as a Vehicle for Topical Antiviral Chemotherapy," *Annals of the New York Academy of Sciences*, pp. 1–14.

*Primary Examiner*—Leonard Schenkman
*Assistant Examiner*—Joseph A. Lipovsky
*Attorney, Agent, or Firm*—J. Rodgers Lunsford, III; Dale Lischer; William R. Cohrs

[57] ABSTRACT

There is disclosed a preparation and method of treating *Acne vulgaris* which comprises topical application of a preparation comprising an antibacterial agent dissolved in DMSO. The antibacterial agents include ara-A, acyclovir, ribavirin, amikacin, cefamandole, cefoxitin, erythromycin, tetracycline, tobramycin, vancomycin, lincomycin, and carbenicillin.

1 Claim, No Drawings

PREPARATION AND METHOD FOR THE TREATMENT OF ACNE

BACKGROUND OF THE INVENTION

This invention relates generally to a preparation and a method for treating acne, and more particularly concerns a preparation containing an antibacterial agent, which when mixed with a solvent carrier agent, is effective in the treatment of acne.

Acne Vulgaris ("acne") is one of the most common diseases afflicting mankind. Acne is a chronic condition involving the pilosebaceous glands of the skin and is characterized by the presence of comedones, papules, pustules, cysts, and/or scarring. The effects of acne vary from slight pitting to extremely disfiguring scars.

Acne is a term used to encompass a broad range of conditions. Researchers have identified a large variety of clinical types of acne. S. B. Frank, *Acne Vulgaris*, ch. 2 (1971). Moreover, acne occurs virtually worldwide except for some populations in the Far East which are free from the disease. Acne typically occurs in adolescents, but acne may appear in children, preadolescents, and adults.

All acne originates in the sebaceous gland and relies on the sebum produced by the sebaceous gland in order to develop. Adult levels of sebum outputs are absolutely a prerequisite for the development of the disease. Excess sebum production is associated with male hormones; consequently castrates do not get acne.

Bacteria, originally named *Bacillus acnes* and now known as *Propionibacterium acnes* ("*P. acnes*"), reproduces anaerobicly in the sebum of the sebaceous gland. There is some reason to believe that *P. acnes* is a major etiologic factor through the products it synthesizes or the biochemical changes it produces in sebum. Those products or biochemical changes appear to be important both to the formation and rupture of the papules. Perhaps the most compelling indication that *P. acnes* is important in producing acne is the therapeutic effect of a variety of antibiotics which tend to moderate the disease by bringing about a reduction in the *P. acnes* population in the sebaceous glands. Also, there is a striking difference in the levels of *P. acnes* in subjects with and without acne.

The prior art discloses that a few antibiotics are helpful in the treatment of acne. G. Plewig and A. M. Kligman, *Acne, Morphogenesis and Treatment*, ch. 28, p. 297–300 (1975). While acknowledging that there is not a complete understanding of how antibiotics work against acne, Plewig et al. report that tetracycline, erythromycin, and lincomycin when administered orally on a long-term basis help in the management of acne. Plewig et al. also state that the goal for treating acne is to avoid long-term antibiotic use and relay instead on topical therapy.

As disclosed in the prior art, the presence of *P. acnes* is important to the development of acne. In vitro tests show that *P. acnes* is extremely susceptible to antibiotics with activity against gram-positive organisms. Yet only a few antibiotics administered orally are helpful in managing acne.

SUMMARY OF THE INVENTION

It is therefore an object of the present invention to provide a preparation for the topical treatment of acne which comprises an antibacterial agent and a solvent carrier agent which, when applied topically to the acne lesions, will translocate through the skin and cellular walls to attack the *P. acnes* and inhibit the replication process.

It is a further object of the present invention to provide a method for treating acne by topical application of a preparation of ara-A (adenine-9- -D-arabinofuranoside), an antibacterial agent, and DMSO (dimethyl sulfoxide), a solvent carrier agent, mixed in proper proportions.

It is also an object of the present invention to provide a method for treating acne by topical application of a preparation of antibiotics, including amikacin, cefamandole, cefoxitin, erythromycin, tetracycline, tobramycin, vancomycin, lincomycin, and carbenicillin, and DMSO mixed in proper proportions.

Other objects and advantages of the invention will become apparent upon reading the following detailed description of the invention.

DETAILED DESCRIPTION OF THE INVENTION

While the invention will be described in connection with a preferred embodiment and method, it will be understood that I do not intend to limit the invention to that embodiment or method. On the contrary, I intend to cover all alternatives, modifications, and equivalents as may be included within the spirit and scope of the invention as defined by the appended claims.

Ara-A is known to have antiviral properties and in some cases to be effective against *Herpes simplex* virus. As described in my earlier filed copending patent application (Ser. No. 463,467, filed Feb. 3, 1983), the combination of ara-A and DMSO is highly effective in the clinical treatment of *Herpes simplex* virus disease including both oral and genital herpes. I have now discovered that a preparation of ara-A and DMSO is effective when applied topically to acne lesions.

Ara-A is active against a broad spectrum of DNA viruses (these are viruses which contain deoxyribonucleic acid as the predominant nucleic acid type) both in vitro and in vivo (in animal models or in man). It is understood that ara-A interferes with the viral DNA synthesis causing inhibition of viral maturation. Specifically ara-A inhibits the enzyme DNA polymerase, an action that suppresses further viral replication.

Bacteria, such as *P. acnes*, like viruses, depend on DNA synthesis in their reproduction process. As a result, ara-A when introduced to *P. acnes* bacteria has the effect of inhibiting the enzyme DNA polymerase of the bacteria thus suppressing further bacterial replication. It is this attribute that apparently explains the effectiveness of the preparation of ara-A and DMSO in the treatment of acne.

DMSO serves three purposes in enhancing the therapeutic action of ara-A in the present invention. First, DMSO allows a concentration of ara-A that is more than twenty times greater than can be achieved with water alone. Second, and perhaps more importantly, DMSO has the unique ability of permeating the interstitial spaces and cell walls to carry the ara-A along with it into the cells of the bacteria. It is this property of DMSO that is apparently responsible for the extraordinary effectiveness of this medication. Third DMSO is an anti-inflammatory agent and has been approved for treating interstitial cystitis. The anti-inflammatory property of DMSO aids in reducing the inflammatory process of acne.

The formulation of the preparation for the treatment of acne of the present invention is not critical, and the preparation is effective over a wide range of concentrations of both ara-A and DMSO. A sample formula that has been used and is effective against acne is as follows:

EXAMPLE 1

Ara-A: 1.0 gm
DMSO: 70.0 ml
Demineralized water: 30.0 ml

The higher the concentration of DMSO in the solvent carrier medium, the greater is the amount of ara-A that can be dissolved. Also, the therapeutic effectiveness of ara-A appears to increase with concentration up to a point. The active concentration range with regard to DMSO is 50 to 100% of the solvent carrier medium. The ara-A range is 1.0 mg/ml to 100 mg/ml. An all encompassing formula, covering all useful concentrations by percentage is:

EXAMPLE 2

Ara-A: 0.1 to 10.0 (of total composition)
DMSO: 50 to 100 (of solvent carrier medium)
Demineralized water: 0 to 50 (of solvent carrier medium)

Another ingredient or component that might be usefully added to the composition is a local anesthetic such as benzocaine or dibucaine which may be incorporated into the medication for local pain control. The medication of the present invention has been prepared and used both ways. It appears that the presence of benzocaine does not impair the effectiveness of the medication. Nor does the benzocaine appear to have any deleterious effect on the patient when administered in DMSO. Also one to two percent high viscosity carboxymethylcellulose, Carbopol (manufactured by Firestone Company, Akron, Ohio), or other suitable gelling agent might be added to the mixture to provide a gel which may be preferred for topical application.

There are no special procedures involved in preparing of the preparation for the treatment of acne of the present invention. The demineralized water and DMSO can be mixed first, and the ara-A (and benzocaine if used) is then dissolved in the DMSO and water solution. The ara-A can be added to the pure DMSO, and water can be added last. When water and DMSO are mixed, the solution becomes warm because there is a positive heat of solution. There is no chemical reaction between ara-A and DMSO under the conditions of preparation. Ara-A can be recovered from the DMSO and water solution virtually 100% as unchanged ara-A.

Regarding toxicity or other side effects on the patient of the proposed preparation, extensive pharmacologic and toxicity studies on ara-A have been carried out in animals and in man. The acute intraparateneal $LD_{50}$ for this drug rages from 3900 to 4500 mg/kg in mice and 3300 to 2500 mg/kg in rats. This dose level indicates a low order of toxicity to a single parenteral dose. The acute oral $LD_{50}$ in both rats and mice is greater than 5000 mg/kg. This amount would be equivalent to more than 750 grams (one and two thirds pound) in an average 150 pound man. It is not possible to demonstrate toxicity through topical application of this compound. In some cases, however, redness and slight irritation has been noted after topical application. A massive acute overdosage of intravenous form of ara-A has been reported without any serious side effects. In the form used in the present invention and with treatment by topical application, it is highly unlikely that any toxic side effects of ara-A would be observed.

DMSO has been studied extensively also, in both animals and humans and is essentially nontoxic. When DMSO is applied to the skin in its undiluted state, it sometimes may cause an itching or burning sensation with redness or rash. This rash, however, usually disappears shortly thereafter with no ill effects. *Annals of the New York Academy of Sciences,* Vol. 243, (1967). S. W. Jacob, E. E. Rosenbaum, and D. C. Wood, eds., Vol. 1, *Dimethyl Sulfoxide,* 99 (1971), and Vol. 243, *Annals of the New York Academy of Sciences,* (1975). In the present invention DMSO is diluted to 70% with demineralized water before ara-A is added. At this concentration, DMSO is usually non-irritating to normal skin.

Treatment of acne with the disclosed preparation should begin as soon as the first sign of the lesion (pimple) is apparent. If treatment is started at this early stage, the acne lesion (pimple) is aborted, and does not develop. Even treatment after pimples, papules, or pustules have appeared helps resolve those lesions two to three days sooner than when left untreated. The medication should be applied every two to four hours for the first two days during waking hours.

In addition to the preferred embodiment described using ara-A as the antibacterial agent, the present invention also encompasses those analogs of ara-A which display significant antibacterial activity by interfering with the DNA synthesis to inhibit bacterial replication. Thus, for example, acyclovir and ribavirin, which are similar to ara-A in that all three are purine analogs, will when mixed with DMSO provide clinical benefits against acne.

In addition to the purine analogs, some antibiotics when mixed with DMSO are also effective in the topical treatment of acne. These antibiotics including, amikacin, cefamandole, cefoxitin, erythromycin, tetracycline, tobramycin, vancomycin, lincomycin, and carbenicillin. The ability of DMSO to carry the antibiotic directly to the site of the *P. acnes* reproduction apparently explains the effectiveness of these antibiotics when administered topically mixed with DMSO as compared to oral administration.

The antibiotic formulation of the preparation for the treatment of acne of the present invention is not critical, and the preparation is effective over a wide range of concentrations of antibiotic and DMSO. Sample antibiotic formulas that are effective against acne are as follows:

EXAMPLE 3

Amikacin: 1.0 gm
DMSO: 70.0 ml
Demineralized water: 30.0 ml

EXAMPLE 4

Carbenicillin: 2.5 gm
DMSO: 70.0 ml
Demineralized water: 30.0 ml

EXAMPLE 5

Cefamandole: 1.5 gm
DMSO: 70.0 ml
Demineralized water: 30.0 ml

EXAMPLE 6

Cefoxitin: 1.5 gm
DMSO: 70.0 ml

Demineralized water: 30.0 ml

EXAMPLE 7

Erythromycin: 0.5 gm
DMSO: 70.0 ml
Demineralized water: 30.0 ml

EXAMPLE 8

Lincomycin: 1.0 gm
DMSO: 70.0 ml
Demineralized water: 30.0 ml

EXAMPLE 9

Tetracycline: 0.5 gm
DMSO: 70.0 ml
Deminerlized water: 30.0 ml

EXAMPLE 10

Tobramycin: 0.5 gm
DMSO: 70.0 ml
Demineralized water: 30.0 ml

EXAMPLE 11

Vancomycin: 0.5 gm
DMSO: 70.0 ml
Demineralized water: 30.0 ml

Furthermore in accordance with the present invention, the antibiotics listed in Examples 3 through 11 can range from 0.1 to 10.0% of the total composition, the DMSO can range from 50 to 100% of the solvent carrier medium, and the demineralized water can range from 0 to 50% of the solvent carrier medium.

The solvent carrier in Examples 3 through 11 may also include propylene glycol up to 10% of the solvent carrier medium. The propylene glycol is useful in enhancing the solubility of the antibiotics.

I claim:

1. A method for treating acne in humans comprising the step of topically applying to acne papules or pustules present on the skin of said humans a preparation comprising a solvent carrier being between 50 percent and 100 percent dimethylsulfoxide which will translocate through the skin and penetrate cell walls and an antibacterial agent being between 0.1 percent and 10.0 percent of the preparation and selected from the group consisting of ara-A, acyclovir, and ribavirin.

* * * * *